(12) United States Patent
Mernoe et al.

(10) Patent No.: US 8,430,847 B2
(45) Date of Patent: Apr. 30, 2013

(54) INFUSION PUMP SYSTEM

(75) Inventors: Morten Mernoe, Sunnyvale, CA (US);
James Causey, Simi Valley, CA (US);
Mitchell Wenger, Sunnyvale, CA (US);
Mark Estes, Sunnyvale, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 0 days.

(21) Appl. No.: 12/817,049

(22) Filed: Jun. 16, 2010

(65) Prior Publication Data

US 2010/0256564 A1 Oct. 7, 2010

Related U.S. Application Data

(63) Continuation of application No. 11/557,910, filed on Nov. 8, 2006.

(60) Provisional application No. 60/734,382, filed on Nov. 8, 2005, provisional application No. 60/758,955, filed on Jan. 13, 2006, provisional application No. 60/771,496, filed on Feb. 8, 2006.

(51) Int. Cl.
*A61M 37/00* (2006.01)

(52) U.S. Cl.
USPC ........ 604/131; 417/477.2; 604/151; 604/156; 604/174; 604/175; 604/177; 604/110; 604/123; 604/132; 604/135; 604/136; 604/142; 604/157; 604/158; 604/161; 604/162; 604/164.01; 604/164.08; 604/198; 604/263; 604/264; 604/273; 604/506; 604/890.1; 604/93.01

(58) Field of Classification Search ................ 417/477.2; 604/131, 151, 156, 174, 175, 177, 110, 123, 604/132, 135, 136, 142, 157, 158, 161, 162, 604/164.01, 164.08, 198, 263, 264, 273, 604/506, 890.1, 93.01
See application file for complete search history.

(56) References Cited

U.S. PATENT DOCUMENTS

| | | | |
|---|---|---|---|
| 2,605,765 | A | 8/1952 | Kollsman |
| 3,688,764 | A | 9/1972 | Reed |
| 3,886,938 | A | 6/1975 | Szabo et al. |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Opposition Brief re: European Patent in EP1951340, mailed Apr. 21, 2010, 38 pages.

(Continued)

*Primary Examiner* — Theodore Stigell
*Assistant Examiner* — Scott Medway
(74) *Attorney, Agent, or Firm* — Thompson Patent Law Offices PC; Craige Thompson

(57) ABSTRACT

An infusion pump system is described that increases patient comfort and convenience. The infusion pump system includes an infusion site interface that is releasably connected to an infusion pump body, and has no tubing associated between the infusion site interface and the pump body. The infusion pump body may include a carrier frame that may be adhered to the skin of a user.

11 Claims, 18 Drawing Sheets

U.S. PATENT DOCUMENTS

| | | |
|---|---|---|
| 4,077,405 A | 3/1978 | Haerten et al. |
| 4,231,368 A | 11/1980 | Becker |
| 4,235,234 A | 11/1980 | Whitney et al. |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,552,561 A | 11/1985 | Eckenhoff et al. |
| 4,734,092 A | 3/1988 | Millerd |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,209,230 A | 5/1993 | Swedlow et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,656,032 A | 8/1997 | Kriesel et al. |
| 5,665,065 A | 9/1997 | Colman et al. |
| 5,672,167 A * | 9/1997 | Athayde et al. ............ 604/892.1 |
| 5,693,018 A | 12/1997 | Kriesel et al. |
| 5,741,216 A | 4/1998 | Hemmingsen et al. |
| 5,772,635 A | 6/1998 | Dastur et al. |
| 5,816,306 A | 10/1998 | Giacomel |
| 5,851,197 A | 12/1998 | Marano et al. |
| 5,852,803 A | 12/1998 | Ashby, III et al. |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,329 B1 * | 10/2002 | Van Antwerp et al. ....... 604/111 |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,537,268 B1 * | 3/2003 | Gibson et al. .............. 604/891.1 |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,685,674 B2 | 2/2004 | Douglas et al. |
| 6,687,546 B2 | 2/2004 | Lebel et al. |
| 6,689,100 B2 | 2/2004 | Connelly et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |

| | | |
|---|---|---|
| 6,945,961 B2 | 9/2005 | Miller et al. |
| 6,948,918 B2 | 9/2005 | Hansen |
| 6,950,708 B2 | 9/2005 | Bowman IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,070,580 B2 | 7/2006 | Nielsen |
| 7,104,972 B2 | 9/2006 | Moller et al. |
| 7,128,727 B2 | 10/2006 | Flaherty et al. |
| 7,133,329 B2 | 11/2006 | Skyggebjerg et al. |
| 7,172,572 B2 * | 2/2007 | Diamond et al. .............. 604/32 |
| 7,232,423 B2 | 6/2007 | Mernoe |
| 7,494,481 B2 | 2/2009 | Moberg et al. |
| 7,641,649 B2 | 1/2010 | Moberg et al. |
| 2001/0056262 A1 | 12/2001 | Cabiri |
| 2002/0004651 A1 | 1/2002 | Ljnggreen et al. |
| 2002/0007154 A1 | 1/2002 | Hansen et al. |
| 2002/0040208 A1 | 4/2002 | Flaherty et al. |
| 2002/0072720 A1 | 6/2002 | Hague et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0216683 A1 | 11/2003 | Shekalim |
| 2003/0216686 A1 * | 11/2003 | Lynch et al. .............. 604/93.01 |
| 2004/0006316 A1 | 1/2004 | Patton |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 * | 6/2004 | Hansen et al. .............. 417/379 |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0158207 A1 | 8/2004 | Hunn et al. |
| 2004/0171983 A1 | 9/2004 | Sparks et al. |
| 2004/0176727 A1 | 9/2004 | Shekalim |
| 2004/0187952 A1 * | 9/2004 | Jones ............................. 141/2 |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0101933 A1 | 5/2005 | Marrs et al. |
| 2005/0107743 A1 | 5/2005 | Fangrow, Jr. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069351 A9 | 3/2006 | Safabash et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0173410 A1 | 8/2006 | Moberg et al. |
| 2006/0178633 A1 | 8/2006 | Garibotto et al. |
| 2006/0184104 A1 | 8/2006 | Cheney et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247574 A1 | 11/2006 | Maule et al. |
| 2006/0247581 A1 | 11/2006 | Pedersen et al. |
| 2006/0253086 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2007/0073228 A1 | 3/2007 | Mernoe et al. |
| 2007/0073236 A1 | 3/2007 | Mernoe et al. |
| 2007/0079836 A1 | 4/2007 | Reghabi et al. |
| 2007/0093786 A1 | 4/2007 | Goldsmith et al. |
| 2007/0124002 A1 | 5/2007 | Estes et al. |
| 2007/0142776 A9 | 6/2007 | Kovelman et al. |
| 2007/0156092 A1 | 7/2007 | Estes et al. |
| 2007/0156094 A1 | 7/2007 | Safabash et al. |
| 2007/0166170 A1 | 7/2007 | Nason et al. |
| 2007/0167905 A1 | 7/2007 | Estes et al. |
| 2007/0167912 A1 | 7/2007 | Causey et al. |
| 2007/0191702 A1 | 8/2007 | Yodfat et al. |
| 2008/0009824 A1 | 1/2008 | Moberg et al. |
| 2008/0045891 A1 | 2/2008 | Maule et al. |
| 2008/0051697 A1 | 2/2008 | Mounce et al. |
| 2008/0051698 A1 | 2/2008 | Mounce et al. |
| 2008/0051714 A1 | 2/2008 | Moberg et al. |
| 2008/0051716 A1 | 2/2008 | Stutz |
| 2008/0051730 A1 | 2/2008 | Bikovsky |
| 2008/0051738 A1 | 2/2008 | Griffin |
| 2008/0077081 A1 | 3/2008 | Mounce et al. |
| 2008/0097326 A1 | 4/2008 | Moberg et al. |
| 2008/0097375 A1 | 4/2008 | Bikovsky |
| 2008/0208627 A1 | 8/2008 | Skyggebjerg |
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0269683 A1 | 10/2008 | Bikovsky |
| 2008/0269687 A1 | 10/2008 | Chong et al. |
| 2008/0319384 A1 | 12/2008 | Yodfat et al. |
| 2008/0319394 A1 | 12/2008 | Yodfat et al. |
| 2008/0319414 A1 | 12/2008 | Yodfat et al. |
| 2008/0319416 A1 | 12/2008 | Yodfat et al. |
| 2009/0036870 A1 | 2/2009 | Mounce et al. |
| 2009/0082728 A1 | 3/2009 | Bikovsky |
| 2009/0198191 A1 | 8/2009 | Chong et al. |
| 2009/0198215 A1 | 8/2009 | Chong et al. |

FOREIGN PATENT DOCUMENTS

| | | |
|---|---|---|
| DE | 19912459 | 9/2000 |
| DE | 102 36 669 A | 2/2004 |
| DK | PA 2004/01893 | 12/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1824536 | 6/2006 |
| EP | 1 754 498 | 2/2007 |
| EP | 1951340 | 5/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |

| | | |
|---|---|---|
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO02/081012 | 10/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | 2005/011779 | 2/2005 |
| WO | WO 2005/039673 | 5/2005 |
| WO | WO 2005/072794 | 8/2005 |
| WO | WO 2005/072795 | 8/2005 |
| WO | WO2006/061354 | 6/2006 |
| WO | WO 2006/105792 | 10/2006 |
| WO | WO 2006/105793 | 10/2006 |
| WO | WO 2006/105794 | 10/2006 |
| WO | WO2007/071255 | 6/2007 |
| WO | WO2007/078992 | 12/2007 |

OTHER PUBLICATIONS

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 04, and JP 11 010036 , Apr. 30, 1999 and Jan. 19, 1999, Toray Ind. Inc.

Accu-Chek Spirit, "Pump Therapy Made for You," Roche, 2006, 6 pages.

Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

The Medtronic Diabetes Connection, 2006, 6 pages.

OmniPod Insulin Management System—Investor Relations—Press Release, Feb. 1, 2005, http://investors.insulet.com/phoenix.zhtml?c=209336&p=irol-newsArticle&ID=988708&highlight=1 page.

OmniPod Quick Start Guide, 2007, 2 pages.

U.S. Appl. No. 11/362,616.

U.S. Appl. No. 60/734,382, filed Nov. 8, 2005, Mernoe, et al.

Oxford Advanced Learners Dictionary, 4th Ed., Oxford University Press, Oxford, 1989. p. 178.

Duden Deutsches Universalworterbuch, Dudenverlag, Mannheim, 1989, p. 822.

Abstract of M. Guamieri et al., J. Neurosc. Meth. 144, 147-152, Jun. 15, 2005.

Propreitor's Counterstatement, EP 1951340B1, mailed Dec. 16, 2010, 20 pages.

Opposition brief, mailed on Oct. 20, 2010, EP Patent No. 1951340, 16 pages.

Opposition brief, mailed on Apr. 21, 2010, EP Patent No. 1951340B1, 33 pages.

European Patent Office Appl. No. 06827657.5, "Summons to Attend Oral Proceedings" including a preliminary non-binding opinion of the opposition division, date Apr. 27, 2012, 7 pgs.

U.S. Appl. No. 60/753,684, filed Dec. 23, 2005.

Submission to EPO in preparation of the oral proceedings, EP1951340, dated Sep. 27, 2012, 38 pages.

Interlocutory decision in Opposition proceedings (Art. 101(3)(a) and 106(2) EPC), 59 pages, dated Feb. 11, 2013, EP application No. 06827657.5.

Provision of a copy of the minutes in accordance with Rule 124(4) EPC, 20 pages, dated Feb. 11, 2013, EP application No. 06827657.5.

* cited by examiner

INFUSION PUMP SYSTEM

CROSS-REFERENCE TO RELATED APPLICATIONS

This application is a continuation of U.S. patent application Ser. No. 11/557,910 filed on Nov. 8, 2006, which claims the benefit of U.S. Provisional Application 60/734,382, filed Nov. 8, 2005, U.S. Provisional Application 60/758,955, filed Jan. 13, 2006, and U.S. Provisional Application 60/771,496, filed Feb. 8, 2006. The disclosures of the prior applications are considered part of and are hereby incorporated in their entirety by reference in the disclosure of this application.

TECHNICAL FIELD

This invention relates to infusion pump systems.

BACKGROUND

An infusion pump may be used to infuse fluids, medication, or nutrients into a patient's body or circulatory system. An infusion pump is generally used intravenously, although subcutaneous, arterial and epidural infusions are occasionally used. Infusion pumps can reliably administer fluids in ways that would be impractically expensive or unreliable if performed manually by nursing staff. For example, infusion pumps can administer 1 mL per hour injections (too small for a drip), injections every minute, injections with repeated boluses requested by the patient up to the maximum number per hour allowed (e.g. in patient-controlled analgesia), or fluids whose volumes vary by the time of day.

As infusion pumps can also produce quite high but controlled pressures, the pumps can inject controlled amounts of fluids subcutaneously (beneath the skin), or epidurally (just within the surface of the central nervous system—a very popular local spinal anesthesia for childbirth).

Conventional infusion pumps rely on disposable infusion sets to link the pump system to an infusion site. These sets generally have a length of tubing between both ends to accommodate the patient's changes to wear position, pump maintenance and programming and to facilitate changing of the catheter system. As pump systems gradually reduce in size and complexity, the tubing becomes tangled as a result of its length making the pumps difficult to use and uncomfortable for the patient.

SUMMARY

A disconnectable, body-worn infusion pump system allows a more convenient attachment method for the user of a body-attached or body-worn pump. The device described herein may adhere to the skin of a wearer. The infusion pump system maintains a fluid path between the wearer and a pump. This path can be intermittently broken and re-established without replacement of the catheter within the body of the user.

An infusion pump system is described that includes an infusion site interface including a soft cannula for penetration of the skin when the interface is installed, and a hub that rises above the upper surface of the interface when the interface is installed, wherein the infusion site interface lacks tubing above the upper surface of the interface, and an infusion pump body, wherein the infusion pump body can be releasably connected to the infusion site interface to form a direct connection between the infusion pump body and the infusion site interface.

The system may include an infusion site interface adhesively attached to the infusion site on a body. The infusion site interface may include a carrier frame having an adhesive on the upper surface, enabling temporary adhesion of the pump body to the upper surface of the carrier frame. The infusion site interface may include a carrier frame, wherein the carrier frame is adhesively connected to a body near an infusion site location, and the carrier frame is connected to the hub. The carrier frame may be connected to the hub via structural supports between the hub and an outer frame. The carrier frame may include a webbing.

The system may include an adhesive on the pump body that enables temporary adhesion of the pump body to another surface. The exit port of the infusion pump body may connect directly to an entry port on the infusion site interface.

The pump body may releasably connect to the infusion site interface using a locking mechanism on the hub of the infusion site interface, or may releasably connect to the infusion site interface using a guide on the hub of the infusion site interface, or may releasably connect to the infusion site interface using the penetration of a pump body exit port through an infusion site interface septum. The pump body exit port may include a needle.

The infusion pump body may include a control system. The infusion site interface may have no tubing external to the skin of a user after installation of the infusion site interface.

A method of operating an infusion pump system is described that includes dispensing medicament from a medicament reservoir in a pump body through a pump body exit port into an infusion site interface, wherein there is a direct connection between the infusion pump body and the infusion site interface during the dispensing, and wherein the pump body is releasably connected to the infusion site interface.

The pump body exit port may include a catheter that penetrates a septum of the infusion site interface. The catheter may include a needle. The pump body exit port may connect directly to an entry port on the infusion site interface. The pump body may releasably connect to the infusion site interface using a locking mechanism, or may releasably connect to the infusion site interface using a guide on the infusion site interface, or may releasably connect to the infusion site interface using only the penetration of the pump body exit port through an infusion site interface septum.

The infusion site interface may be adhesively attached to the infusion site on a body. The pump body may be adhesively attached near the infusion site. The pump body may be adhesively attached to an upper surface of the infusion site interface. The pump body may be adhesively attached using a single layer adhesive.

An infusion pump system is described that includes an infusion site interface including a soft cannula for penetration of the skin when the interface is installed, a carrier frame that can be adhesively attached to a body surface, and a hub that is connected to the carrier frame and rises above the carrier frame when the interface is installed, and an infusion pump body, wherein the infusion pump body can be connected, detached, and re-connected to the infusion site interface as desired to form a direct connection between the infusion pump body and the infusion site interface.

An infusion pump system is described that includes an infusion site interface including a soft cannula for penetration of the skin when the interface is installed, a carrier frame that can be adhesively attached to a body surface, and a hub that is connected to the carrier frame and rises above the carrier frame when the interface is installed, and an infusion pump body that can be releasably connected to the infusion site interface, forming a direct connection between the infusion pump body and the infusion site interface, and an adhesive surface on the infusion pump body.

The adhesive surface may be used to attach the infusion pump body to the infusion site interface. The adhesive surface may be used to attach the infusion pump body near an infusion site.

As used herein, the term "direct connection" refers to a connection that does not include any tubing or similar intermediary between the two endpoints of the direct connection.

As used herein, the term "medicament" generally refers to all fluids, medication, drugs, nutrients, biomaterials, chemicals, or other materials that may be dispensed by an infusion pump.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

An infusion pump system is described that increases patient comfort and convenience. The infusion pump system includes an infusion pump body and an infusion site interface. The infusion pump body is releasably connected to the infusion site interface, and therefore there is no associated tubing between the infusion pump body and the infusion site interface. The infusion pump body also includes a housing that may be adhered to the skin of a user.

Figure 1:
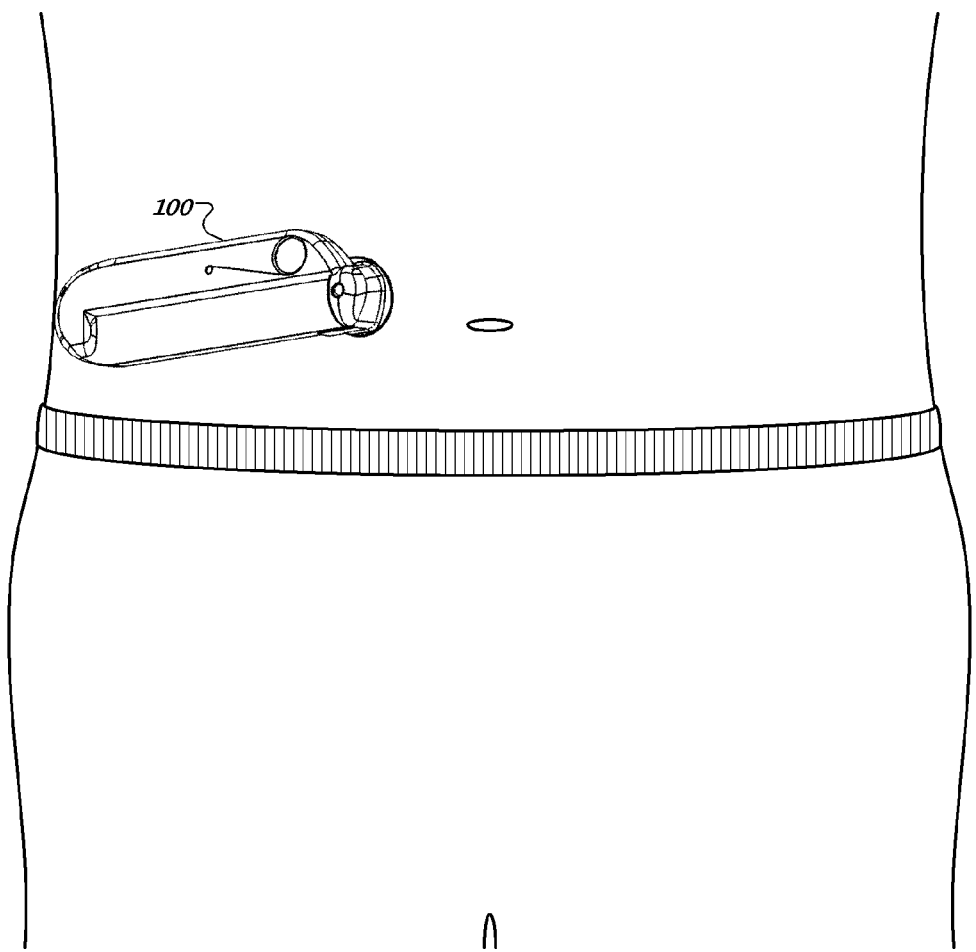
FIG. 1 is an illustration of an assembled and connected infusion pump system attached to a human torso.

FIG. 1 shows a view of an assembled infusion pump system 100 attached to a human torso. The infusion pump system 100 may be used to infuse a medicament directly into an infusion site. A complete flow path is formed from a medicament reservoir within the infusion pump system 100 to the infusion site.

Figure 2:
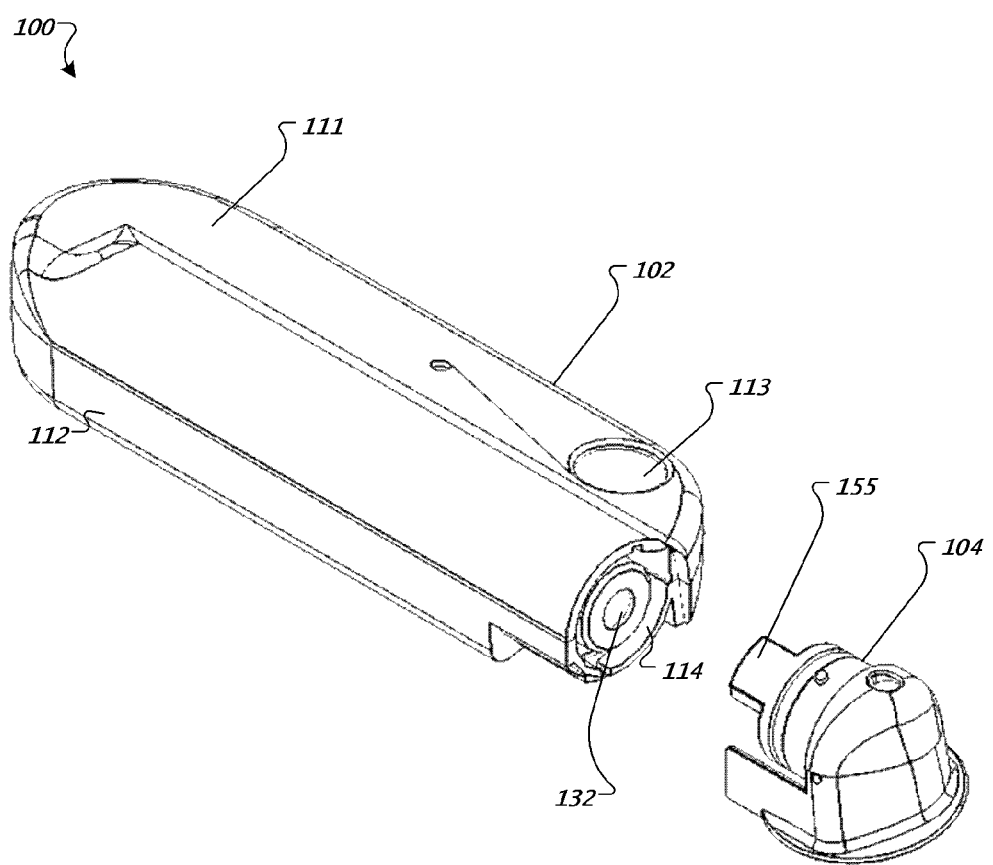
FIG. 2 is an illustration of an example of an infusion pump system, including an infusion pump body detached from an infusion site interface.
Figure 3:
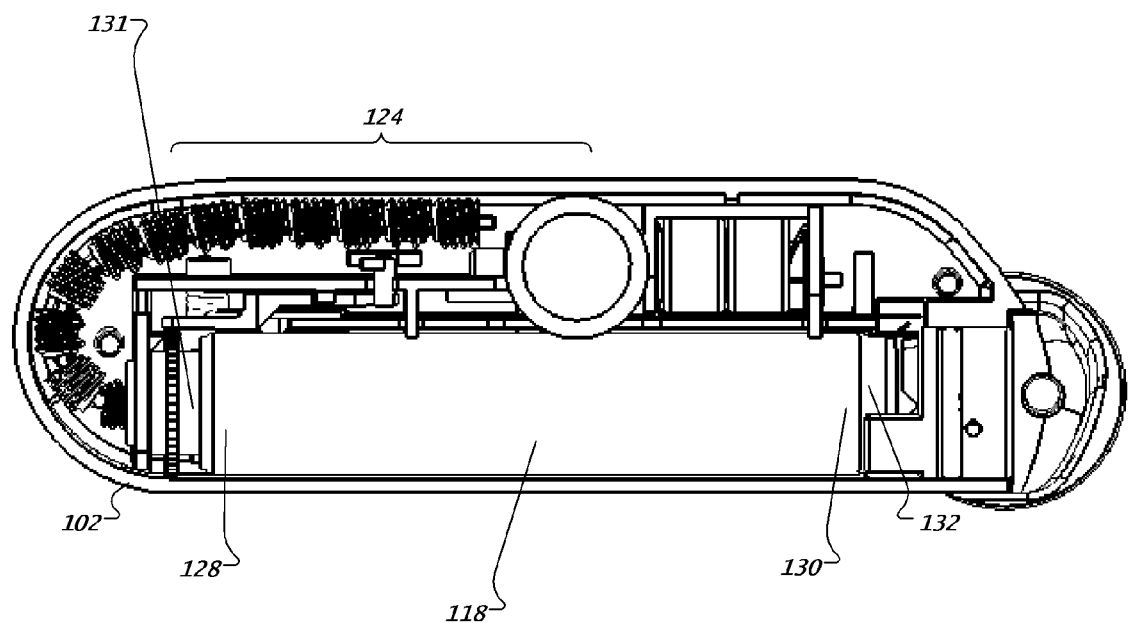
FIG. 3 is a cross-sectional illustration of an assembled and connected infusion pump system.

FIGS. 2-3 are illustrations of a self-contained infusion pump system including an infusion site interface. FIG. 2 shows a disassembled view of the infusion pump system 100, including a pump body 102 and an infusion site interface 104. FIG. 3 shows a cut-away cross-section view of the assembled infusion pump system 100. The component parts illustrated in these views create a complete, self contained medicine infusion pump system when assembled.

Returning to FIG. 2, the infusion pump body has an upper housing 111 and a lower housing 112 which define a periphery in which the pump mechanisms reside. The lower housing 112 may be adhered to a user's skin by means of an adhesive system. The upper and lower housings 111, 112 may include openings or penetrations 114 for attachment and guidance of the infusion site interface 104 to the pump body 102. Additionally, the openings 114 may allow for installation of a reservoir contained within the pump body 102. One or more buttons 113 may be used to enter user requests into the pump system.

As can be seen in FIG. 3, mechanisms that are contained in the pump body 102 may include a reservoir 118, a drive mechanism 124, and a control system. The reservoir 118 includes a distal end 128 and a proximal end 130. The reservoir 118 may be cylindrical in geometry with the distal end 128 sealed by a moveable plunger 131 of matching geometry as the reservoir 118. The proximal end 130 of the reservoir 118 may be closed by a reservoir septum 132. In some embodiments, the reservoir septum 132 may be formed of a self-sealing material, such as silicone or rubber. In other embodiments the proximal end 130 of the reservoir 118 may be closed by a valve or other device. The drive mechanism 124 may be actuated to apply pressure internal to the reservoir 118 so that a medicament contained within the reservoir 118 may be dispensed out of the reservoir 118. In one embodiment, the medicament may be pushed through a device that pierces the reservoir septum 132. In other embodiments, the medicament may be pushed through a valve or other device at the proximal end 130 of the reservoir 118. The actuation of the drive mechanism 124 may be governed by the control mechanism. The geometry of the reservoir 118 has been shown as cylindrical for illustrative purposes only and the reservoir 118 is geometry independent.

In one embodiment, a reservoir 118 containing a medicament may be installed in the pump body 102 via an opening in the pump body 114. The infusion pump body may be prepared for use after installation of the infusion site interface 104 at a body location. In some embodiments, the infusion pump body may be prepared for use by inserting a reservoir 118 of medicament in the infusion pump body 102. For example, a generally cylindrical and geometrically matched medicament reservoir 118 is inserted into the vacant pump cavity. In another embodiment, the reservoir might be installed by separating the pump body, such as by separating upper and lower housings. In another embodiment, the reservoir might be pre-loaded into the pump body, and require no user loading. Examples of medicaments that may be contained in the medicament reservoir 188 may include insulin, pain relief drugs, hormone therapy, blood pressure treatments, anti-emetics, osteoporosis treatments, or other injectable medicines or liquids.

Figure 4:
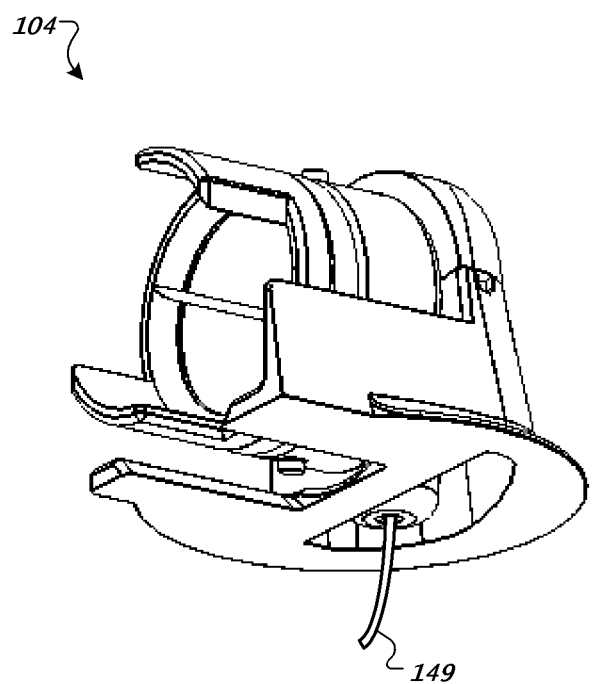
FIG. 4 shows an assembled view of one example of an infusion site interface.
Figure 5:
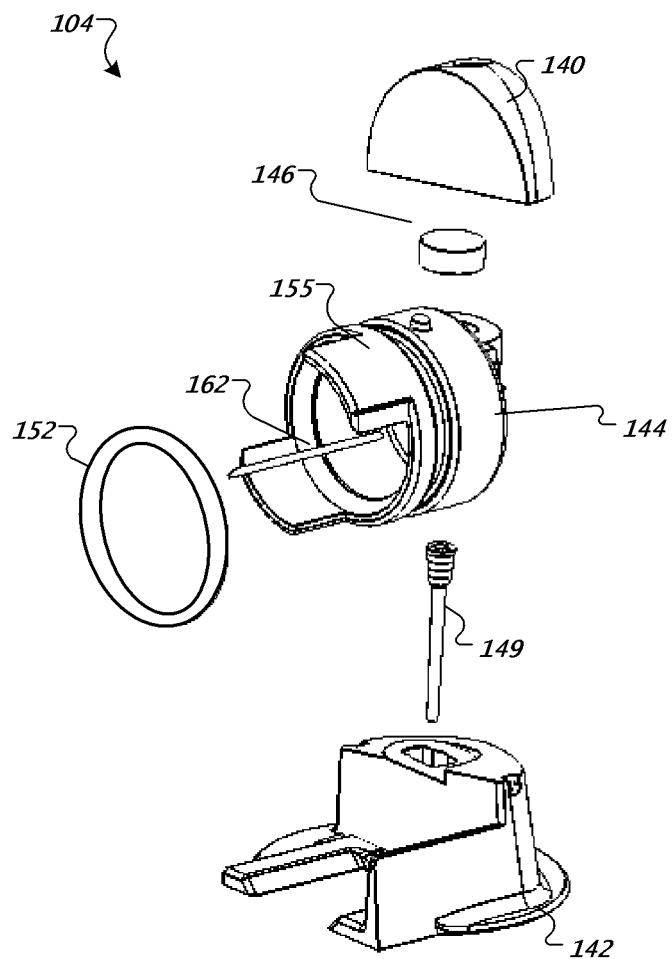
FIG. 5 shows a component view of one example of an infusion site interface.

FIGS. 4 and 5 show assembled and component views of one example of an infusion site interface 104. The infusion site interface may also be referred to as a catheter head system. The infusion site interface 104 provides for continuous or intermittent subcutaneous fluid infusion and is comprised of an upper housing 140, a lower housing 142, a hub 144 having a hollow chamber, an infusion site interface septum 146, a catheter of biocompatible material 149, and an O-ring 152 for sealing the exterior surface 155 of the hub 144 against the interior surface of the pump body 102 associated with the opening 114 of the pump body. The catheter 149 may be used for indwelling in a user after installation of the infusion site interface 104 at a location on the body. The catheter 149 also defines a through passage for passing a medicament from the infusion pump system into a body. The infusion site interface 104 provides for the continuous fluid path between the reservoir 118 and the user.

A continuous fluid path may be formed by connecting one side of the hub 144 to the pump body. One side of the hub 144 may be equipped with a septum piercing device 162 that penetrates the reservoir septum 132 (shown in FIG. 3), enabling medicament to enter the hub. In one embodiment, the medicament may enter a chamber or junction within the hub 144. Medicament may flow from the hub 144 through the catheter 149 and into the user. Typically, the infusion site interface 104 is equipped on a side generally tangent to the septum piercing device 162 and coplanar to a user's skin. The biocompatible catheter 149 may be used for subcutaneous infusion of medicine to a user. Thus, the septum piercing device 162 of the infusion site interface 104 may initiate a pathway for medicament by penetration of the reservoir septum 132 during attachment of the pump body 102 to the infusion site interface 104. During treatment, medicament may traverse from the reservoir 118 through the septum piercing device 162, through the hub 144 and catheter 149, and into the user.

Referring again to FIG. 2, the infusion site interface 104 may be attached to the pump system 102 by insertion of the generally cylindrical exterior surface 155 of the hub 144 of the catheter head system 104 into the geometrically matched opening 114 of the pump body 102. In some embodiments, the exterior surface of infusion site interface 104 may contain alignment features of geometry such that the infusion site interface 104 may be attached in a single orientation or discreet set of orientations into matching mating features in the pump body 102. The alignment feature(s) on the exterior surface of the hub 144 may allow the infusion site interface 104 to be securely attached to the pump body 102, preventing unintended separation of the two systems.

In another embodiment, the pump system 102 may attach to the infusion site interface 104 using another method or device which allows for the secure attachment of the infusion site interface 104 to the pump body 102. In one approach, the secure attachment may be in the form of a locking ring which securely and releasably locks the infusion site interface 104 to the pump system 102. In another approach, the secure attachment may be in the form of a Luer-lock connection. In another approach, the secure attachment may be created by a mechanism or method which is detachable from the completed system, such as flexible connector. In another approach, the secure attachment may be in the form of replaceable locking tabs on the upper housing 111, the lower housing 112 or infusion site interface 104. When locked, the tabs on the infusion site interface 104 may engage features on the pump body 102 to prevent the accidental release of the infusion site interface 104. Alternatively, locking tabs on the pump body 102 may engage features on the infusion site interface 104 to prevent accidental releases. The infusion pump body may be directly connected to the infusion site interface, such that there is no tubing or other intermediate between the pump body and the infusion site interface.

Figure 6:
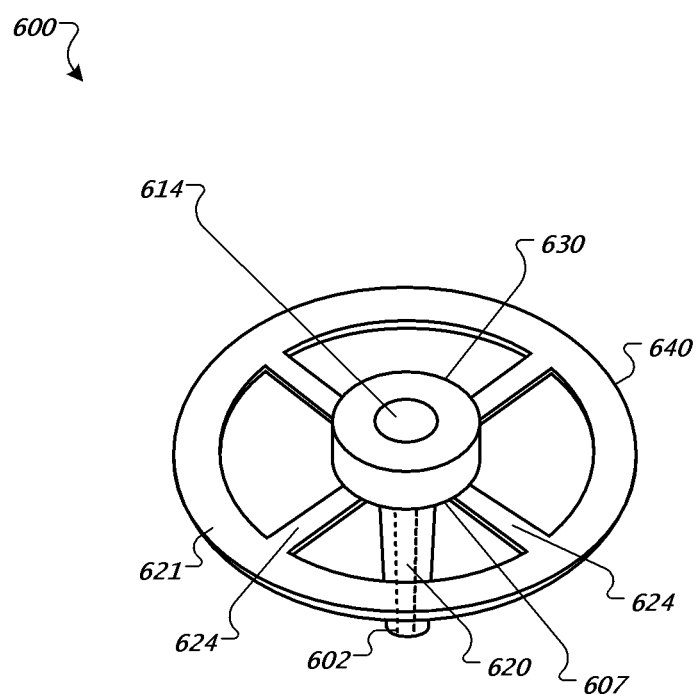
FIG. 6 is an illustration of one example of an infusion site interface.
Figure 7:
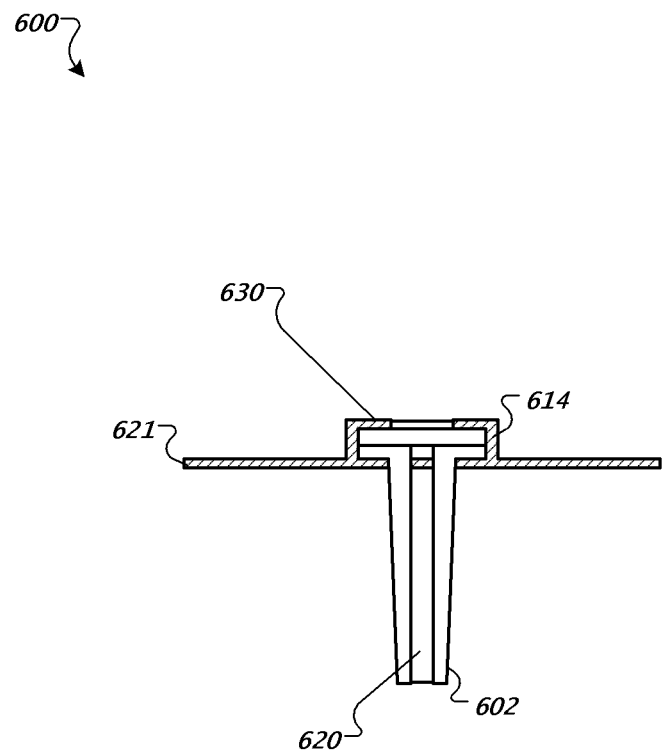
FIG. 7 is a cross-section view of the infusion site interface shown in FIG. 6.

FIG. 6 shows one example of an infusion site interface 600. FIG. 7 shows a cross-section view of the infusion site interface 600 shown in FIG. 6.

The infusion site interface 600 includes a soft cannula 602 of biocompatible material that may be inserted into the body of a user. The cannula 602 is attached at its upper or proximal end to an annular sealing flange 607 that forms the center of a carrier frame 640. The cannula 602 also defines a central channel 620. The annular sealing flange 607 may be attached coaxially to the lower or distal surface of an inner ring or hub 614. Together, these elements provide for the creation of a continuous fluid flow path from the orifice of the hub 614 through to the cannula 602. These elements may also form the confines of an intermediate chamber in the hub 614 that connects to the channel 320 in the cannula 602. The hub 614 defines a central orifice that may be closed by a septum 630 that seals the fluid path of the hub 614 and cannula 602 from the outside world.

The infusion site interface 600 may also include a carrier frame 640. The carrier frame 640 may include as components an outer frame member 621 and one or more structural supports 624. The outer frame 621 may be attached to the hub 614 by one or more structural supports 624. The structural supports 624 may be configured to be radial spokes, curved supporting members, or other configurations. In various embodiments, there may be zero, one, or multiple structural supports 624. The components forming the carrier frame 640 may be made of a rigid, semi-rigid, or flexible material which may be adhered to the body by a skin adhesive system. The carrier frame may also include a flexible mesh or other material between the hub 614, outer frame member 621 and structural supports 624. When present, the flexible mesh or other material may improve the adhesion of the infusion site interface 600 to a treatment location on a body. The flexible mesh may also assist in attaching, detaching, or handling the infusion site interface 600.

The outer frame member 621 may be of size and shape to permit convenient placement on the body. The outer frame member 621 may be of sufficient rigidity to maintain secure location of the cannula 602 in the body of the wearer, and act to prevent the infusion site interface 600 from changing position or detaching from the desired location. The outer frame member 621 may be of sufficient flexibility to maintain wearer comfort, and maintain attachment of the cannula to the wearer during the normal wear duration.

The cannula 602 may be a biocompatible plastic tube inserted subcutaneously in the body of the wearer to create a fluid path from a pump device to a location within the body of the wearer. The cannula 602 may be rigidly or flexibly attached to the hub 614 of the frame. Generally, the cannula 602 is maintained at a location within the body of the wearer by the adhesion of the carrier frame of the adhesion site interface 600 to the body of the wearer. The infusion site interface may be designed such that there is no tubing that extends external of the body after the infusion site interface is in place. Thus, the infusion site interface may be located on a surface of a body, with a soft cannula descending to a tissue location. The infusion site interface may also include a carrier frame that is adhesively attached to the body, holding the infusion site interface in place, and a hub that extends above the surface of the of the carrier frame for attachment of a pump body.

The septum 630 provides a penetrable barrier or seal from the inserted cannula 602 to the outside world. The septum 630 may be of a size sufficient to allow the insertion of a drug delivery needle (as described below) or a similar drug delivery conduit. The entry of the drug delivery conduit into the cannula 602 may be perpendicular to the skin surface or at a suitably convenient angle. The septum 630 may be formed of a self-sealing material such as rubber or silicone.

The infusion site interface 600 may also include a leak detection mechanism, whereby positive indication is provided to the wearer of the infusion site system 600 that a compromise in the fluid path has occurred. This indication can be by visual or tactile means either through color change or a means for dermal stimulation at the site.

Figure 8:
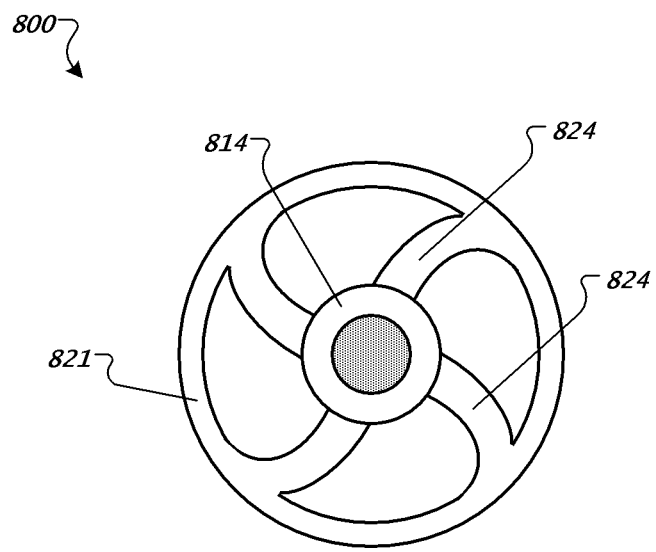
FIG. 8 is a top view illustration of another example of an infusion site interface.

FIG. 8 shows a top view of one embodiment of an infusion site interface 800. The infusion site interface 800 shown is similar to infusion site interface 600 in FIGS. 6 and 7, with the exception that the hub 814 is attached to the outer frame member 821 by a plurality of structural supports 824 that are curved radial spokes. In some embodiments, the carrier frame may also include a flexible mesh or other material between the hub 814, outer frame member 821 and structural supports 824.

Figure 9A:
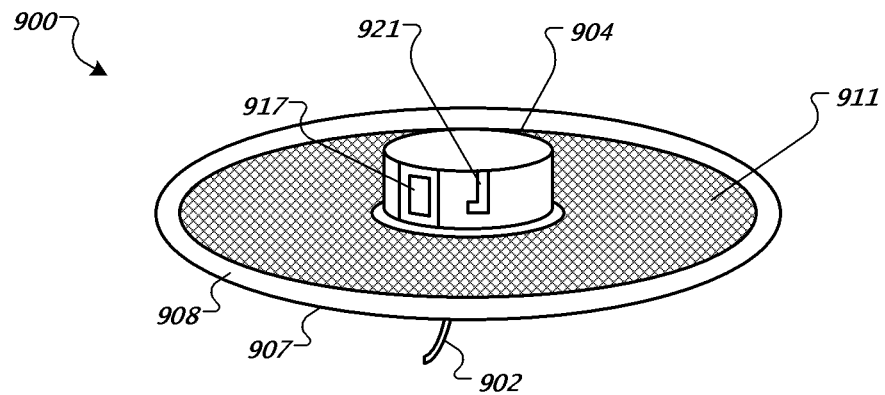
FIG. 9A is an illustration of another example of an infusion site interface having an access port.

FIG. 9A shows another example of an embodiment of an infusion site interface 900. The infusion site interface 900 includes a central hub 904 and a cannula 902. The cannula 902 may be formed of a soft biocompatible material, and is designed for insertion into the body of a user. The central hub 904 includes an access port 917 and locking features 921. The access port 917 connects to the cannula 902 such that medicaments that pass through the access port 917 pass through and into the cannula 902 for infusion into a user. The locking features 921 may be used to affix an infusion pump body to the infusion site Interface. A covering which normally seals against the access port 917 to prevent foreign materials from entering the infusion site system 900 opens when an infusion pump body is attached to allow medicaments pumped from the infusion pump body to pass into the infusion site interface.

The infusion site interface 900 may also include a carrier frame 907. The carrier frame 907 may include an outer frame member 908 and a flexible material 911. The central hub 904 may be connected to the outer frame member 908 by the flexible material 911. The flexible material 911 may be formed of a mesh or other material. The carrier frame 907 formed by the outer frame member 908 and flexible material 911 may adhere to the body by a conventional adhesive system.

Figure 9B:
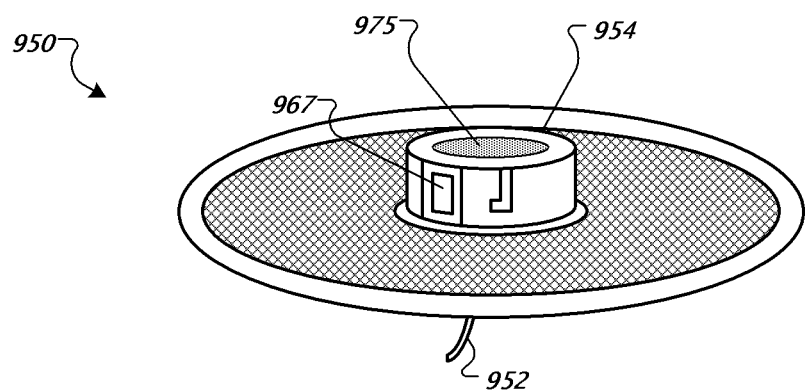
FIG. 9B is an illustration of another example of an infusion site interface having an access port and a septum.

FIG. 9B shows another example embodiment of an infusion site interface 950, similar to the infusion site interface of FIG. 9A. The infusion site interface 950 shown in FIG. 9B also includes a septum 975 located on the top surface of the hub 954. In this embodiment, the access port 967 or the septum 975 may be used to supply a medicament from an infusion pump body to the cannula 952 for infusion into a user.

Figure 10:
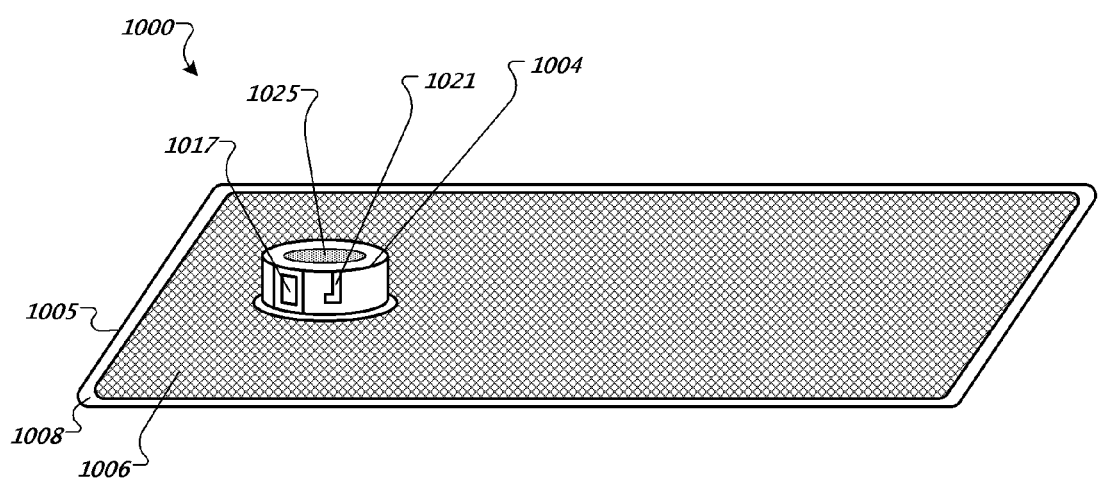
FIG. 10 is an illustration of another example of an infusion site interface.

FIG. 10 shows another example embodiment of an infusion site interface 1000. Infusion site interface 1000 includes a hub 1004 and a carrier frame 1005. The carrier frame 1005 includes an outer frame member 1008 and a flexible mesh 1006. The outer frame member 1008 is affixed to the hub 1004 by the flexible mesh 1006. The carrier frame 1008 may be in a rectangular shape, as shown in FIG. 10, or may have alternate shapes, such as a circle, square, o ellipse, or may have other regular or irregular shapes. Adhesive may be applied to the bottom surface of the carrier frame, including the flexible mesh 1006 and the outer frame 1008, and may be used to affix the infusion site system to a user's body.

The hub 1004 includes an access port 1017, a septum 1025, and locking features 1021. The locking features 1021 may be used to affix an infusion pump system to the infusion site system 1000. The access port 1017 and septum 1025 connect to a cannula (not shown) such that medicaments from an infusion pump body which pass through the access port 1017 or septum 1025 pass through and into the cannula for infusion into a user.

Figure 11:
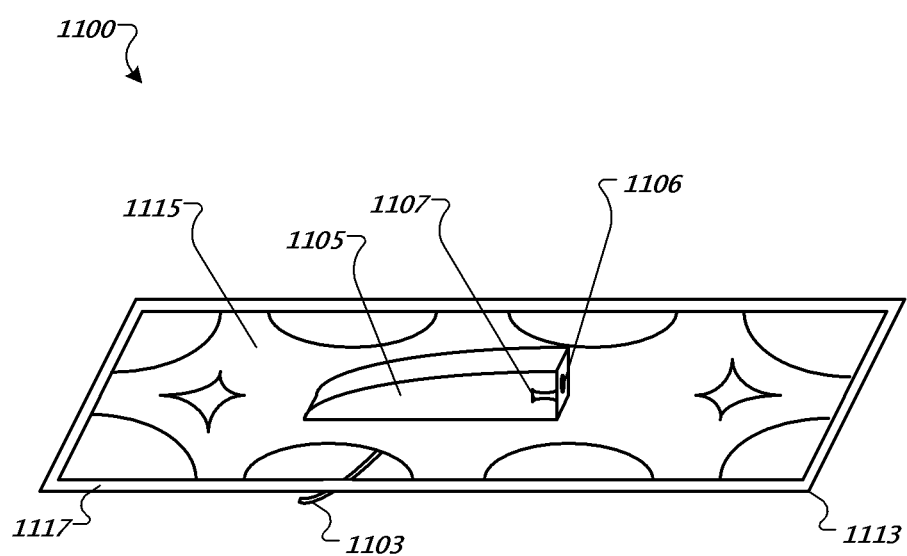
FIG. 11 is an illustration of another example of an infusion site interface.

FIG. 11 shows another example embodiment of an infusion site interface 1100. Infusion site interface 1100 includes a cannula 1103, a central body hub 1105, and a carrier frame 1113. The cannula 1103 is attached to the central body hub 1105, and may be accessed by an infusion pump body via a septum 1106. A locking mechanism 1107 may be incorporated into the central body hub 1105 and may be used to attach an infusion pump body to the infusion site interface 1100. The carrier frame 1113 may include an outer frame member 1008 which is connected to the central body hub 1105 by a structural support 1115. In this embodiment, the structural support is configured as webbing. The webbing may be rigid, semi-rigid, or flexible. In some embodiments, the carrier frame 1113 may also include a flexible mesh or other material between the central body hub 1105, outer frame member 1008, and webbing 1115. The carrier frame 1113 may be adhered to a user's body via the outer frame member 1117, webbing 1115, and if present, the optional mesh or other material. In other embodiments, the central body hub 1105 may have one or more guiding members to guide an infusion pump body for attachment to the infusion pump interface 1100.

The skin adhesive system used with the infusion site systems described above may include a variety of systems, methods, and materials. In one embodiment, the skin adhesive system may be a flexible membrane with skin compatible adhesive capable of removably securing an infusion site interface to the skin of a user. In another embodiment, a flexible membrane may have a skin compatible adhesive on a first surface and a device compatible adhesive on a second surface. In other embodiments, the skin adhesive system may include an adhesive composed of a single layer material that is adhesive to both the user's skin surface and the infusion site interface. Variously, the adhesive material may be a gel layer, a liquid layer that dries after contact, or other material. The precise size and placement of adhesive may be dependant on the application. Typically, the adhesion of the infusion site interface to a user's skin may also include adhesion of a carrier frame to the user's skin.

FIGS. 12A-12D illustrate how adhesives may be used with an infusion pump body 1200 to establish a fluid path from the infusion pump system 1200 to an infusion site system without direct mechanical coupling, thereby creating a "floating" fit wherein the flexibility of the infusion pump system including the infusion pump body and the infusion site interface is greatly increased.

Figure 12A:
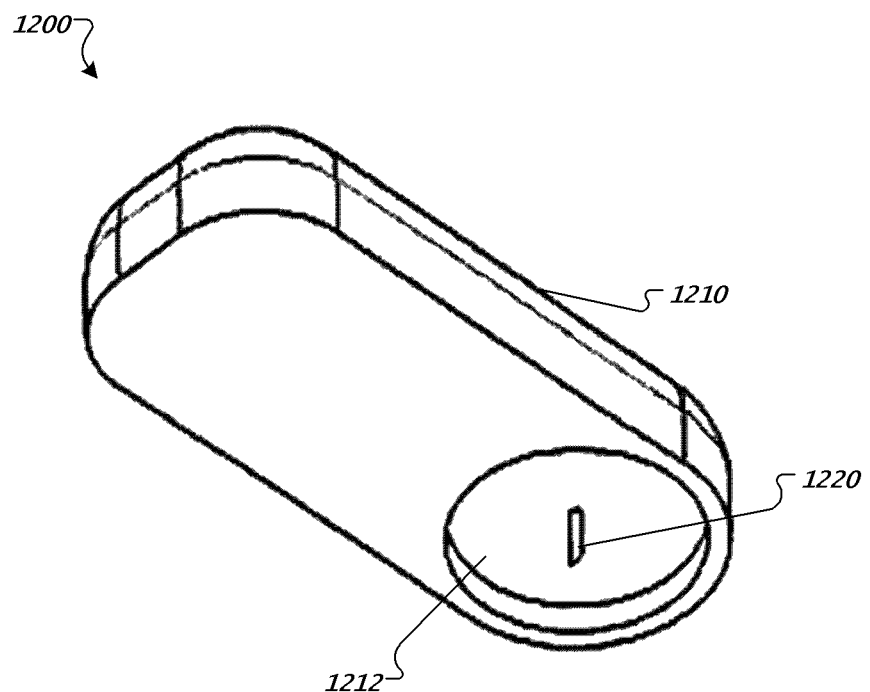
FIG. 12A illustrates an infusion pump system 1200 which may be used with an infusion site interface such as the ones shown in FIG. 6.

FIG. 12A illustrates an infusion pump body 1200 which may be used with various infusion site interfaces, such as the ones shown in FIG. 6. The infusion pump body 1200 includes a casing 1210 which contains a reservoir and pumping mechanism. The infusion body 1200 also includes an infusion site docking area 1212 with a septum piercing device 1220 that may provide a direct fluid path from the reservoir to the infusion site interface. The septum piercing device 1220 also serves as the exit port of the infusion pump body. The pumping mechanism including the pump housing 1210 may cause a medicament in the reservoir to flow through the septum piercing device 1220 and pass into an infusion site interface.

A connection between the infusion pump body and an infusion site interface may be created by the septum piercing device penetrating a septum of the infusion site interface. This may be accomplished without the direct attachment of the infusion pump housing 1210 to the infusion pump interface. The infusion pump body would then be able to move relative to the infusion site interface, and move as the user moved. The infusion pump body may use manual or automatic methods to establish the fluid connection after placement of the infusion pump system 1200 on the body. In some embodiments the infusion site interface and the infusion site docking area 1212 may include corresponding guiding members, such that the pump casing 1210 may be guided onto the infusion site interface. This embodiment would allow for vertical flexibility, while restricting horizontal motion between the pump body 1200 and the infusion site interface.

The adhesive system described above may be sufficient size and capability to adhere the infusion site interface to the skin of the user. In some embodiments, the adhesive system may also have sufficient size and capability to also adhere the infusion pump body to the skin of the wearer or to the infusion site interface. A release liner may be used with the adhesive system. Prior to application of an adhesive, a release liner may cover exposed adhesives to prevent unintentional adhesion. Immediately before or during application, the release liner may be removed to expose the adhesive layer for use.

Figure 12B:
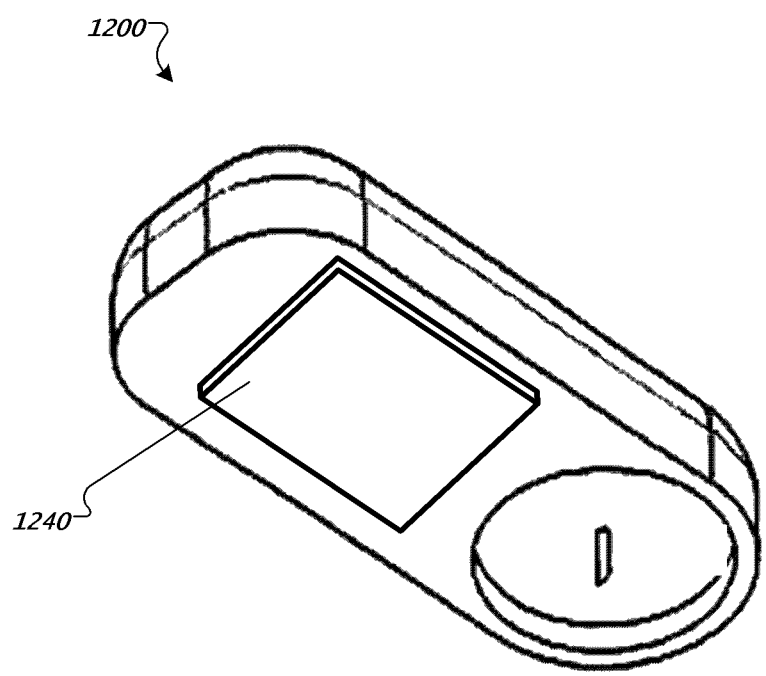
FIGS. 12B-D are illustrations of examples of infusion pump systems with adhesives for affixing near an infusion site.

FIG. 12B shows one embodiment of an adhesive system. In this adhesive system, the adhesive 1240 covers a portion of the bottom of the infusion pump body 1200.

Figure 12C:
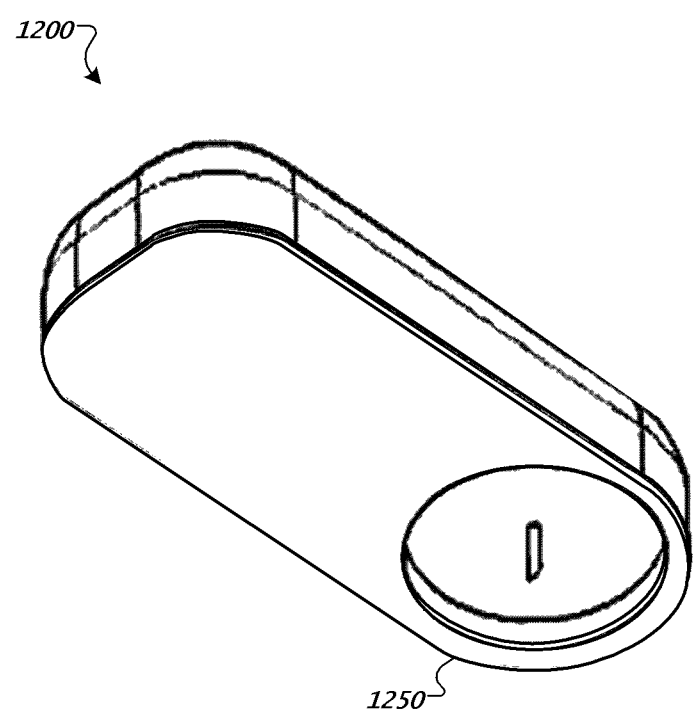

FIG. 12C shows another embodiment of an adhesive system, in which adhesive 1250 covers the entire bottom of the infusion pump body 1200.

Figure 12D:
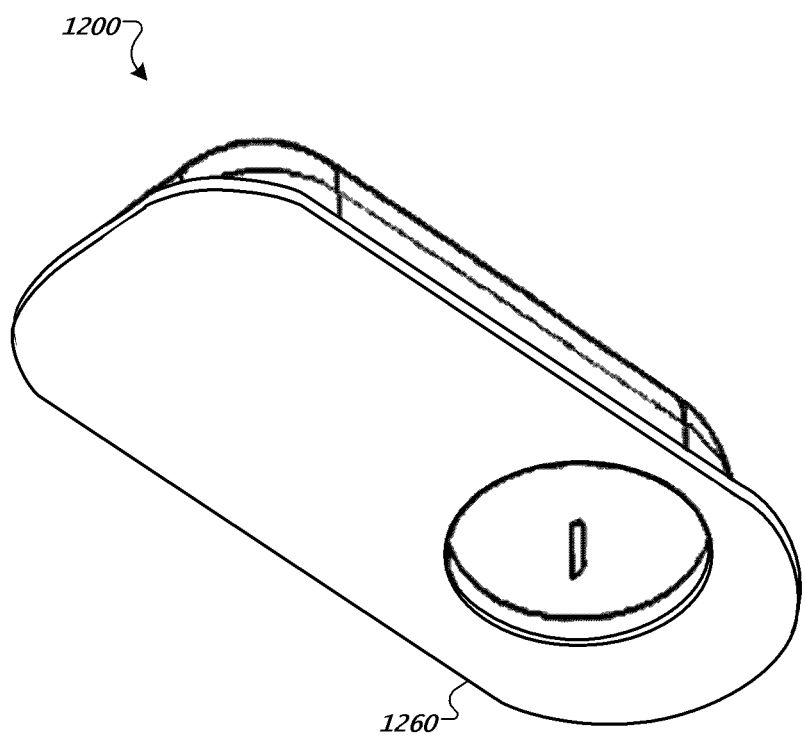

FIG. 12D shows another embodiment of an adhesive system, in which adhesive 1260 extends past the edges of the infusion pump system 1200.

In some embodiments, the adhesive may be formed as a planar substrate of material to which adhesive may be applied to one or both sides. A first adhesive, such as hydrocolloid or synthetic rubber, may be applied to the skin contacting surface for extended adhesion to human skin in all conditions. A second adhesive, such as acrylic, synthetic rubber or any other type of adhesive that is appropriate for the characteristics of the adhesive system, may be applied to the device contacting surface. In some embodiments, the adhesive system may include a flexible agent with a skin compatible adhesive on a first surface and a device compatible adhesive on a second surface.

The variation in thickness of the carrier across the surface of adhesion is dependant on the material selected for the carrier and the mechanical properties desired. In some embodiments, the carrier thickness will be in the range of 0.1 mm to 1 mm. For example, a carrier frame including an adhesive patch designed to extend 2.5 cm from the periphery of an infusion site hub may, for example, have an adhesive thickness of 0.5 mm at region of contact with the infusion site interface hub, and a thickness that decreases to a thickness of 0.2 mm at the edges. In some embodiments, the carrier frame of an infusion site interface may be designed to stretch, allowing greater comfort for the user and better adhesion for the device. Both linear and non-linear adhesive thickness changes are possible.

In some embodiments, a single adhesive layer or coating may be applied directly to skin-contacting surfaces of the infusion pump body. Suitable adhesives include hydrocolloid, acrylic, synthetic rubber or other type of adhesive that is appropriate for the characteristics of the device and user skin.

In various embodiments, the adhesive system may also include compounds to reduce or modify the discomfort associated with attachment of the infusion site interface, or the pump body to the skin. These compounds include, but are not limited to, compounds intended to reduce irritation, inflammation and itching. The compounds may be included in the manufacture of the adhesive or the carrier material, or subsequently an adhesive that is manufactured with these properties specifically integrated into the chemical composition may be applied to the device after manufacturing.

Figure 13A:
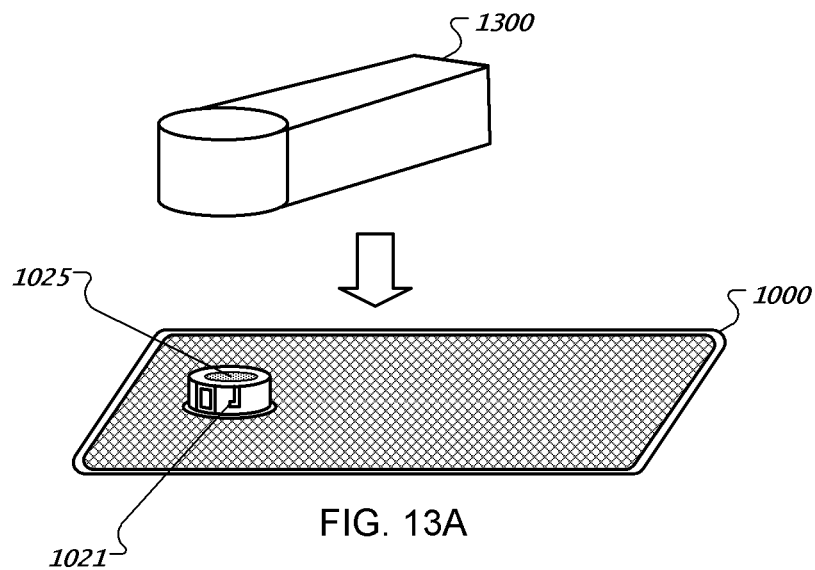
FIGS. 13A-C are illustrations depicting steps of one method that can be used to attach an infusion pump system to an infusion site interface.
Figure 13B:
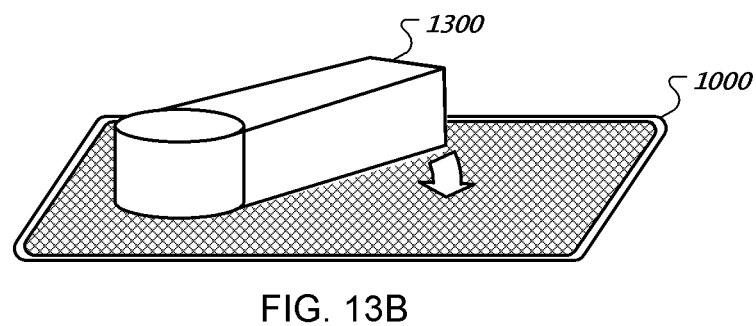
Figure 13C:
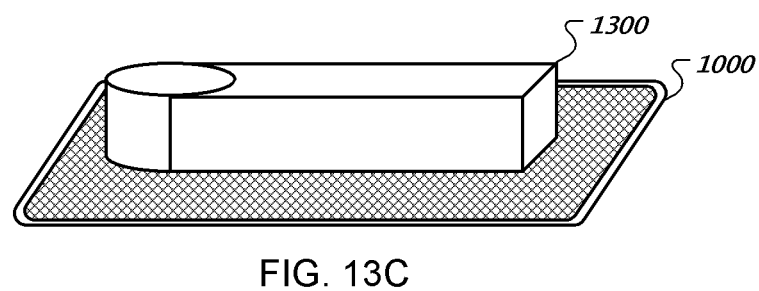

FIGS. 13A-C depict an example of an infusion pump body 1300 with a locking attachment mechanism being attached to the infusion site interface 1000. In FIG. 13A, the infusion pump body 1300 is aligned with a locking collar in the infusion pump body 1300 such that locking features 1021 match up with corresponding features in the locking collar. Pressing the infusion pump system down onto the infusion site system causes a septum piercing device to pierce the septum 1025. In some embodiments, the attachment mechanism connecting the infusion pump body 1300 to the infusion site interface 1000 may be a Luer lock.

FIG. 13B shows a twisting motion used to lock the infusion pump body 1300 onto the infusion site interface 1000. FIG. 13C shows the complete infusion pump system including the infusion pump body 1300 locked to the infusion site interface 1000 via the locking features 1021. In some embodiments, the infusion site interface 1000 includes an adhesive on the top surface of the infusion site interface. In such a case, the pump body 1300 would also be adhesively attached to the infusion site interface, creating a tighter connection between the components of the infusion pump system. In other embodiments, the top surface of the infusion site interface 1000 and the bottom surface of the infusion pump body 1300 may include a mechanical adhesion system. In such a system, the pump body 1300 would be mechanically adhered to the infusion site interface 1000, also creating a tighter connection. An example of a mechanical adhesion system that may be used includes a Velcro adhesive system, or other mechanical adhesion.

Figure 13D:
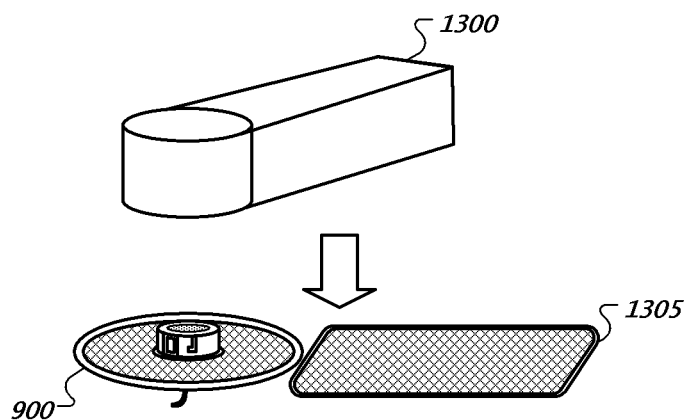
FIGS. 13D-F are illustrations depicting steps of one method that can be used to attach an infusion pump system to an infusion site system.
Figure 13E:
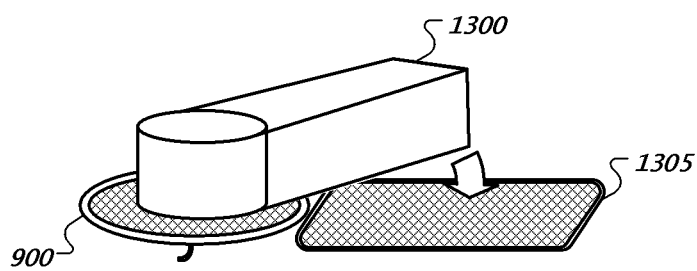
Figure 13F:
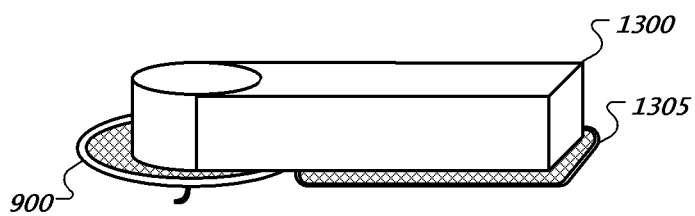

FIGS. 13D-E depict another example of an infusion pump body 1300 with a locking attachment mechanism being attached to the infusion site interface 1000. Similar steps to FIGS. 13A-C are shown, with a different infusion site interface. In this example, infusion site interface 900 is used to affix the infusion pump body 1300 to the user's body. In addition, an additional mesh 1305 is used to secure the infusion pump body 1300 to the user's body after attachment to the infusion site interface. In various embodiments, the additional mesh 1305 may include an adhesive on the top surface for attachment to the pump body 1300, or may include a mechanical adhesion system used in conjunction with other components on the infusion pump body 1300.

In some embodiments, an infusion pump system may be attached to an infusion site system with an insert and twist method, or alternately a detent fit or user activated locking lever or securing mechanism whereby the frame of the infusion site system is mechanically coupled to the body of the infusion pump system.

In other embodiments, the alignment method may use guide features to connect a pump body with an infusion site interface. These guide features may employ geometries or shapes for the infusion site interface in which complimentary geometries and shapes are provided on the infusion pump body to maintain alignment.

In other embodiments, the mechanical attachment of infusion pump body to the infusion site interface 600 may be effected without mechanical locking. The infusion site interface may include a mechanism for the alignment of the infusion pump body, with adhesion of the pump body to the skin being the only method employed to retain the exit port of the infusion pump body within the infusion site interface to maintain fluid path continuity.

Figure 14:
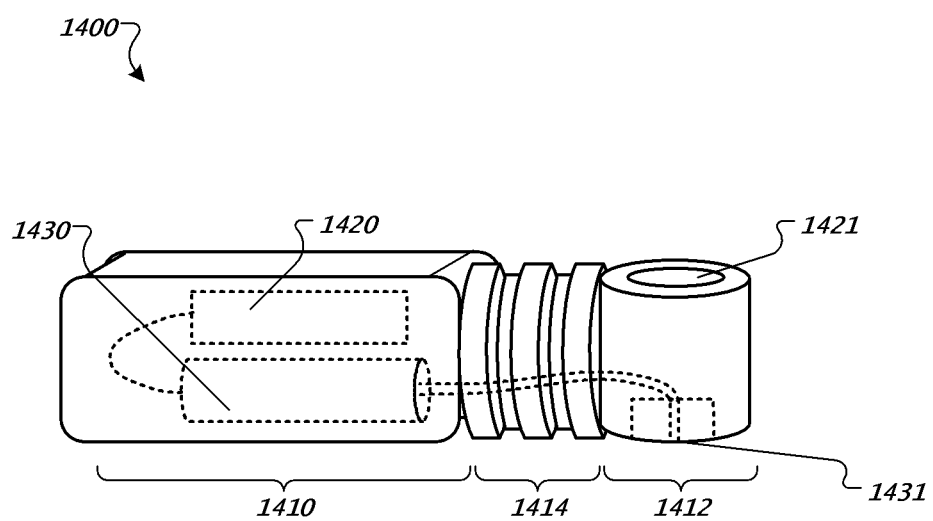
FIG. 14 depicts an alternate embodiment of an infusion pump system 1400 with a flexible neck for use with an infusion site interface.

FIG. 14 depicts an alternate embodiment of an infusion pump body for use with an infusion site system. The infusion pump body 1400 includes a pump body reservoir section 1410, a flexible neck 1414, and an infusion pump head 1412. The infusion pump head 1412 is used to connect to an infusion site interface, such as those described earlier. The flexible neck 1414 allows the pump body 1410 and infusion site interface to move semi-independently relative to each other when attached together. The pump body reservoir section 1410 includes a pumping mechanism 1420 and a reservoir 1430 containing a medicament to be infused. The reservoir 1430 is connected to an exit port 1431 on the infusion pump head 1412 such that a medicament in the reservoir may flow directly from the reservoir to an attached infusion site interface. The exit port 1431 may be formed of a septum piercing device.

In some embodiments, the infusion pump body 1400 may have a window 1421 which may be used to access the infusion site. Such a window may allow for inspection or care of the infusion site without removing the infusion pump body 1400. In some embodiments, the window 1421 may be able to be opened or moved aside, allowing for access to the infusion site or infusion site interface. For example, this might allow for injection of an additional or different medicament using the same infusion site interface.

While several specific embodiments and variations have been described herein, it will be appreciated that other variations and modifications may be encompassed within the scope of the present invention, and that structural and functional equivalents to the various components and structures described herein will occur to those skilled in the pertinent arts. For example, the physical shape and size of the individual component parts, as described herein, are exemplary only, and other shapes and configurations will readily suggest themselves. Likewise, various ways may be found to attach the infusion site system to the pump and or to provide a separate locking mechanism. Furthermore, the configurations of the mechanisms and elements described herein are likewise exemplary only. The extent of this document should be deemed to include any device that exemplifies the concepts described herein and these and other variations and modifications that may suggest themselves to those skilled in the pertinent arts are considered to be within the spirit and scope of the present invention. Accordingly, other embodiments are within the scope of the following claims.

What is claimed is:

1. A medicine infusion pump system, comprising:
    an infusion site interface structure that is adhesively attachable a skin surface, the infusion site interface structure comprising: a frame with a lower surface facing toward the skin surface, a soft cannula coupled to the frame for extension below the lower surface of the frame and configured for subcutaneously insertion through the skin surface to at least partially define a fluid path, and a septum arranged in the fluid path and having a major surface that extends generally parallel to the lower surface of the frame; and
    an infusion pump device is releasably attachable to the frame of the infusion site interface structure so that a needle extending from the infusion pump device penetrates the septum of the infusion site interface, wherein when the infusion pump device is releasably attached to the frame of the infusion site interface structure, the infusion pump device dispenses a medicine through the fluid path from a medicine reservoir housed in the infusion pump device, through the penetrated septum of the infusion site interface structure, and through the soft cannula extending below the lower surface of the frame, wherein the fluid path is configured to be intermittently broken and re-established when the infusion pump device which houses the medicine reservoir is temporarily disconnected from and reconnected with from infusion site structure while the infusion site interface structure is adhesively attached the skin surface.

2. The system of claim 1, wherein the septum of the infusion site interface structure is arranged in the fluid path in a position above a generally upward facing surface of the frame which is opposite from the lower surface of the frame.

3. The system of claim 2, wherein the infusion pump device covers over the generally upward facing surface of the frame of the infusion site interface when the infusion pump device is releasably attached to the frame of the infusion site interface structure.

4. The system of claim 3, wherein the needle of the infusion pump device extends downwardly through an upper face of the septum such that the needle extends generally perpendicular to the skin surface when the needle penetrates the septum of the infusion site interface structure.

5. The system of claim 4, wherein the frame of the infusion site interface structure comprises an inner ring hub that carries the septum and an outer wall that is spaced apart from the inner ring hub and surrounds the inner ring hub.

6. The system of claim 5, wherein the soft cannula is rigidly attached to the inner ring hub of the frame of the infusion site interface structure.

7. The system of claim 6, wherein when the infusion pump device is releasably attached to the frame of the infusion site interface structure, the needle of the infusion pump device is aligned with the inner ring hub of the frame of the infusion site interface structure.

8. The system of claim 1, wherein when the infusion pump device is releasably attached to the frame of the infusion site interface structure, a mechanical coupling between the infusion pump device and the frame of the infusion site interface structure provides a direct connection such that the fluid path is free of tubing.

9. The system of claim 1, wherein a mechanical coupling between the infusion pump device and the frame of the infusion site interface structure is secured by a detent fit.

10. The system of claim 1, wherein a mechanical coupling between the infusion pump device and the frame of the infusion site interface structure is secured by an insert-and-rotate fit.

11. The system of claim 1, further comprising a leak detection mechanism that provides a positive indication when the fluid path is compromised by a leak.

* * * * *